(12) United States Patent
DeBusk et al.

(10) Patent No.: US 10,061,892 B2
(45) Date of Patent: Aug. 28, 2018

(54) APPARATUS AND METHOD FOR PROVIDING SELECTIVELY ZOOMED IMAGE OF MEDICAL ITEM TRAY

(71) Applicant: DeRoyal Industries, Inc., Powell, TN (US)

(72) Inventors: Brian C. DeBusk, Knoxville, TN (US); Mary E. Kaylor, Chattanooga, TN (US)

(73) Assignee: DeRoyal Industries, Inc., Powell, TN (US)

( * ) Notice: Subject to any disclaimer, the term of this patent is extended or adjusted under 35 U.S.C. 154(b) by 476 days.

(21) Appl. No.: 15/041,546

(22) Filed: Feb. 11, 2016

(65) Prior Publication Data

US 2017/0235878 A1    Aug. 17, 2017

(51) Int. Cl.
| | | |
|---|---|---|
| *G16H 40/20* | (2018.01) | |
| *G06K 7/10* | (2006.01) | |
| *G06F 19/00* | (2018.01) | |

(52) U.S. Cl.
CPC ....... *G06F 19/321* (2013.01); *G06K 7/10366* (2013.01); *G16H 40/20* (2018.01)

(58) Field of Classification Search
CPC ... G06F 19/321; G16H 40/20; G06K 7/10366
See application file for complete search history.

(56) References Cited

U.S. PATENT DOCUMENTS

| | | | | |
|---|---|---|---|---|
| 9,842,189 | B2 * | 12/2017 | Caputo | G06Q 10/087 |
| 9,847,044 | B1 * | 12/2017 | Foster | G09B 23/28 |
| 2007/0284428 | A1 * | 12/2007 | Cambre | G09B 23/28 |
| | | | | 235/375 |
| 2011/0246219 | A1 * | 10/2011 | Smith | G06Q 10/087 |
| | | | | 705/2 |
| 2012/0316987 | A1 * | 12/2012 | DeBusk | G06Q 10/08 |
| | | | | 705/26.8 |

* cited by examiner

*Primary Examiner* — Eliza A Lam
(74) *Attorney, Agent, or Firm* — Luedeka Neely Group, PC (57) ABSTRACT

Medical item identification information is stored in association with information indicating locations at which medical items are placed in a medical item tray. An RFID reader acquires tray identification information from an RFID tag on the tray. An RFID reader also acquires item identification information from an RFID tag on the medical item to be placed in the tray. A database stores medical item identification information in association with tray identification information and tray zone information. The tray zone information indicates particular zones of the tray in which particular items are to be placed. A computer processor processes the medical item identification information, the tray identification information and the tray zone information, and executes instructions to generate a first image depicting a type of medical item tray as indicated by the tray identification information, and a second image that depicts a zoomed in portion of the first image as indicated by the tray zone information.

18 Claims, 4 Drawing Sheets

APPARATUS AND METHOD FOR PROVIDING SELECTIVELY ZOOMED IMAGE OF MEDICAL ITEM TRAY

FIELD

This invention relates to the field of managing inventories of medical items. More particularly, this invention relates to a system for storing medical item identification information in association with coordinates of particular locations of specific medical items in a medical item tray.

BACKGROUND

Traditionally, small medical items that may be used in a medical procedure are stored in designated slots or receptacles in a medical item tray. Such trays can be difficult and time consuming to manage. Some medical items, such as implant screws, are rather small and usually have no identification information printed on them. Typically, there are multiple quantities and sizes of such screws to manage. When such a medical item is removed from its original packaging to be placed in a tray, the item's packaging and other manufacturing information are usually separated from the item and discarded. Some medical items in a tray may be used and replaced frequently, while others may reside untouched in the tray for years.

There is currently no method for maintaining serialized identification information for medical items in a tray that have been separated from their packaging, or for providing traceability for such medical items in the event of a recall.

What is needed, therefore, is a system for visually designating and assigning a particular location in a medical item tray in which to place a specific medical item while restocking the tray, and for associating the serialized identification information of each medical item with its assigned location in the tray.

SUMMARY

The above and other needs are met by a method for storing medical item identification information in association with information indicating locations at which medical items are disposed in a medical item tray. A preferred embodiment of the method includes the following steps:
 (a) acquiring tray identification information from an identification device attached to the medical item tray;
 (b) displaying a first image on a display device, wherein the first image depicts a medical item tray of a type indicated by the tray identification information;
 (c) acquiring medical item identification information from an identification device attached to a medical item that is to be placed in the medical item tray or to a wrapper of the medical item;
 (d) based on the medical item identification information, acquiring tray zone information indicating a zone of the medical item tray in which the medical item is to be placed; and
 (e) displaying a second image on the display device, wherein the second image depicts a portion of the first image corresponding to the zone of the medical item tray indicated by the tray zone information.

In some embodiments, the method also includes:
 (f) selecting a hotspot in the second image corresponding to a location in the medical item tray in which the medical item is to be placed;
 (g) placing the medical item into the location in the medical item tray corresponding to the hotspot selected in step (f); and
 (h) in a medical item information database, associating the medical item identification information with:
  the tray identification information; and
  tray coordinate information corresponding to the location.

Another embodiment of the method includes the following steps:
 (a) acquiring tray identification information from an identification device attached to the medical item tray;
 (b) displaying a first image on a display device, wherein the first image depicts a medical item tray of a type indicated by the tray identification information;
 (c) accessing a medical item information database to determine whether any medical item disposed in the medical item tray identified by the tray identification information has been recalled or is beyond an expiration date;
 (d) based on the medical item identification information, acquiring tray zone information from the medical item information database, the tray zone information indicating a zone of the medical item tray in which is located a recalled or expired medical item;
 (e) displaying a second image on the display device, wherein the second image depicts a portion of the first image corresponding to the zone of the medical item tray indicated by the tray zone information;
 (f) displaying a graphical indicator in the second image, wherein the graphical indicator designates a hotspot in the second image corresponding to a location in the medical item tray in which a recalled or expired medical item is disposed;
 (g) selecting the hotspot designated by the graphical indicator;
 (h) removing the recalled or expired medical item from the medical item tray; and
 (i) in the medical item information database, disassociating the medical item identification information of the recalled or expired medical item from tray coordinate information corresponding to the location designated by the hotspot selected in step (g).

In another aspect, the invention provides an apparatus for storing medical item identification information in association with information indicating locations at which medical items are disposed in a medical item tray. A preferred embodiment of the apparatus includes readers that are operable to acquire tray identification information from an identification device attached to the medical item tray. The readers also acquire medical item identification information from an identification device attached to a medical item that is to be placed in the medical item tray or to a wrapper of the medical item. The apparatus includes a medical item information database that stores medical item identification information in association with tray identification information and tray zone information. The tray zone information indicates particular zones of the medical item tray in which particular medical items are to be placed. The apparatus also includes a computer processor that is in communication with the readers and the medical item information database. The computer processor processes the medical item identification information, the tray identification information and the tray zone information, and executes instructions to generate a first image that depicts a medical item tray of a type indicated by the tray identification information, and generate a second image that depicts a portion of the first image corresponding to a zone of the medical item tray indicated by the tray zone information. A display device displays the first and second images.

In some embodiments, the computer processor executes instructions to generate the second image as a zoomed-in portion of the first image.

In some embodiments, the identification device attached to the wrapper of the medical item is an RFID tag, and the apparatus includes a shielded enclosure having an internal space for receiving the wrapper of the medical item. The shielded enclosure is configured to attenuate radio frequency signals emanated from RFID tags disposed outside the shielded enclosure to levels that are substantially undetectable within the internal space. An RFID antenna that is disposed within the internal space of the shielded enclosure receives a radio frequency signal emanated from an RFID tag attached to the wrapper disposed within the internal space. The radio frequency signal contains the medical item identification information encoded in the RFID tag. The readers preferably include an RFID reader that is electrically connected to the RFID antenna. The RFID reader decodes the medical item identification information contained in the radio frequency signal emanated from the RFID tag.

In some embodiments the computer processor executes instructions to generate the second image including a hotspot corresponding to a location in the medical item tray in which the medical item is to be placed. A user input device is used to select the hotspot in the second image to generate a hotspot signal. The computer processor executes instructions based on the hotspot signal to communicate with the medical item information database to cause the medical item identification information to be associated with the tray identification information and tray coordinate information corresponding to the location.

In some embodiments, the user input device is a touch screen incorporated into the display device.

In some embodiments, the computer processor executes instructions to generate a graphic indicator that is displayed in the second image to designate the hotspot.

In some embodiments, the tray coordinate information comprises X-Y coordinates or row-column coordinates.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

As the term is used herein, a "medical item" is an item, material, substance, or piece of durable medical equipment (DME) that is used or consumed during the performance of a medical procedure. For example, sponges, gloves and drapes are medical items. A surgical implant, such as a plate, rod or screw, is another example of a medical item.

As the term is used herein, a "set" of medical items refers to a collection of medical items that are packaged together for use during a particular medical procedure. In some embodiments, the set of items are packaged in a tray that has a designated location in the tray for each item in the set. However, it will be appreciated that the set of items may be packaged in containers other than trays. As the terms are used herein, "set" and "tray" both refer to a collection of medical items.

As the term is used herein, a "wrapper" encompasses all manner of containers and packaging, sterile or non-sterile, in which a medical item is or has been enclosed. The term "wrapper" also includes a label, hang tag, or other such device that may be attached to a medical item without completely enclosing the item. The term "wrapper" further includes packaging for a sterile-wrapped set of medical items, such as a tray of implants and supplies for use in a surgical procedure, wherein an RFID tag is attached to the tray. Generally, anything that may function to associate an RFID tag with a medical item or a set of medical items is encompassed by the term "wrapper."

Each medical item preferably has a unique item identifier encoded in a machine-readable code in an RFID tag, a QR code, a bar code, or a combination thereof attached to the medical item or its wrapper. In some embodiments, an RFID tag and a QR code are combined in a single label applied to the medical item or its wrapper.

In a preferred embodiment, each wrapper includes an RFID tag attached thereto or embedded therein. Ultra High Frequency (UHF) passive RFID tags are preferred for this application, as they may be interrogated from up to about 30 centimeters to about 30 feet away. In preferred embodiments, each RFID tag is encoded with a unique item identification number for the particular medical item associated with the wrapper. An item information database associates each item identification number with item-specific information, such as the manufacturer part number, item description, serial number, tray slot coordinates, vendor, cost, Latex content, expiration date, and inventory location. Additionally or alternatively, the RFID tag may be encoded with item-specific information as set forth in Unique Device Identification (UDI) standards set by the U.S. Food and Drug Administration (FDA).

In some embodiments, item-specific information encoded in RFID tags on medical items may be used to generate alerts for medical personnel. For example, an alert may be generated if information encoded in an RFID tag indicates that an item's useful lifetime has expired or the item is from a lot that has been recalled by the manufacturer.

As the term is used herein, a "scan" for RFID tags refers to operations performed by an RFID reader to transmit signals and receive signals from RFID tags that are in range of the RFID reader and its associated antenna(s).

Figure 1:
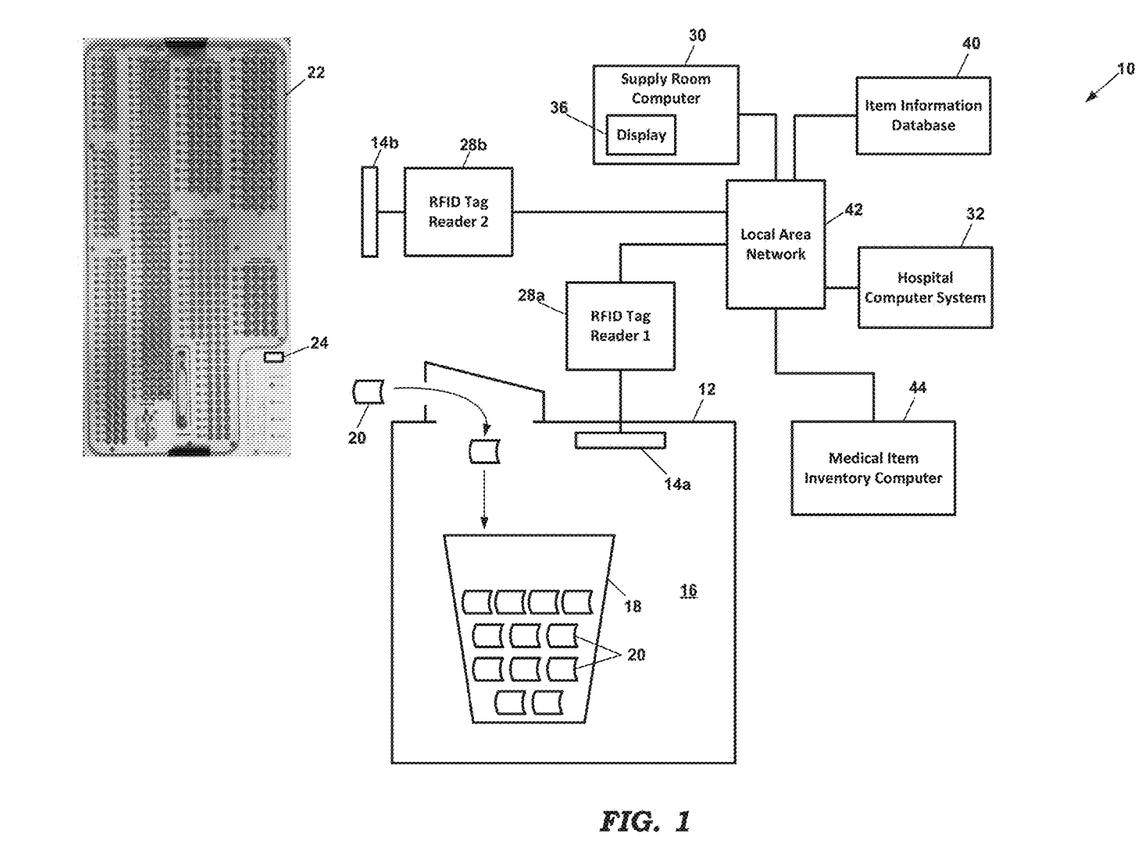
FIG. 1 depicts an embodiment of a system for storing medical item identification information in association with location information indicating specific locations of medical items in a medical item tray.

As shown in FIG. 1, a preferred embodiment of a system 10 for performing inventory functions related to medical items includes a shielded enclosure 12 having a space 16 that is large enough to receive a waste bin 18. Disposed within the enclosure 12 are one or more RFID antennas 14*a*, such as Laird 5×5 inch Mini Far Field antennas (model number S9025PLNF) having left-hand circular polarization and operating in the 902-928 MHz frequency range. The RFID antenna 14*a* is electrically connected, such as via a coaxial cable, to an RFID tag reader 28a. In a preferred embodiment, the RFID tag reader 28a is an Impinj® Speedway® model R420.

As the term is used herein, "shielded enclosure" means the enclosure 12 is designed to prevent the antenna 14a from receiving RFID signals from RFID tags located outside the enclosure 12 at a signal-to-noise ratio high enough to trigger detection of those outside RFID tags. For purposes of this disclosure, "shielded" does not mean that absolutely all RF energy has to be blocked from entering the enclosure, as this may require unnecessary levels of shielding.

In the preferred embodiment, an opening 24 is provided in the top of the enclosure that is large enough to receive wrappers or containers 20 from which medical items have been removed. After medical items are removed from their wrappers 20, the wrappers 20 are dropped through the opening 24 in the enclosure 12 where they are received into the waste bin 18. When the wrappers 20 enter the enclosure 12, the RFID tags on the wrappers 20 are detected and read by the reader 28a. It will be appreciated that a waste bin 18 is not absolutely necessary for this process. However, the use of a waste bin 18 makes collection and removal of the wrappers 20 easier.

Also shown in FIG. 1 is an exemplary set of medical items disposed in a tray 22. In the example of FIG. 1, the tray 22 contains implant screws for use in a medical procedure. As depicted in greater detail in the images shown in FIGS. 3A-B and 4A-B, each screw or other medical item in the tray 22 is held in a slot at a designated location. Each designated location is uniquely defined by a set of coordinates that are preferably stored in an item information database 40.

Attached to the tray 22 is an encoded tray identification device 24, which may be a barcode, a Quick Response (QR) code, or an RFID tag, that uniquely identifies the tray. A preferred embodiment of the system 10 includes a second RFID antenna 14b that is electrically connected, such as via a coaxial cable, to a second RFID tag reader 28b, such as an Impinj® Speedway® model R420. In embodiments wherein the encoded device 24 on the tray 22 is an RFID tag, the RFID tag reader 28b detects and reads the encoded device 24 to identify the specific tray to be processed. In alternative embodiments wherein the encoded device 24 is a barcode or QR code, the system 10 includes a barcode reader or QR code reader to read the encoded device 24.

The RFID tag readers 28a and 28b are electrically connected via a local area network (LAN) 42 to a medical item inventory computer 44, which may be a server computer, desktop computer, laptop computer, tablet computer or other mobile computing device. Alternatively, the electrical connection between the RFID tag readers 28a and 28b and the computer 44 is via a Universal Serial Bus (USB) interface.

Preferred embodiments include a supply room computer 30 having a display screen 36. The supply room computer 30 may be a laptop, desktop or tablet computer that is assigned to a particular supply room. In a preferred embodiment, the supply room computer 30 is a tablet computer in which the display screen 36 is also a user input device, such as a touch screen for receiving input from a user. In alternative embodiments, the supply room computer 30 includes a user input device that is separate from the display screen 36, such as a mouse or touch pad.

The supply room computer 30 is preferably in communication with the medical item inventory computer 44 via a communication network, such as the LAN 42. The supply room computer 30 may also be in communication with a hospital computer system 32 via a communication network, such as the LAN 42. In preferred embodiments, the hospital computer system 32 manages medical item inventories, operating room scheduling, patient records, insurance reimbursement/payment functions, and admission/discharge/transfer (ADT) records. The hospital computer system 32 may also include or be connected to an electronic data interchange server, such as a J.D. Edwards/Oracle server, that implements electronic commerce transactions between the hospital and medical item suppliers.

Figure 2:
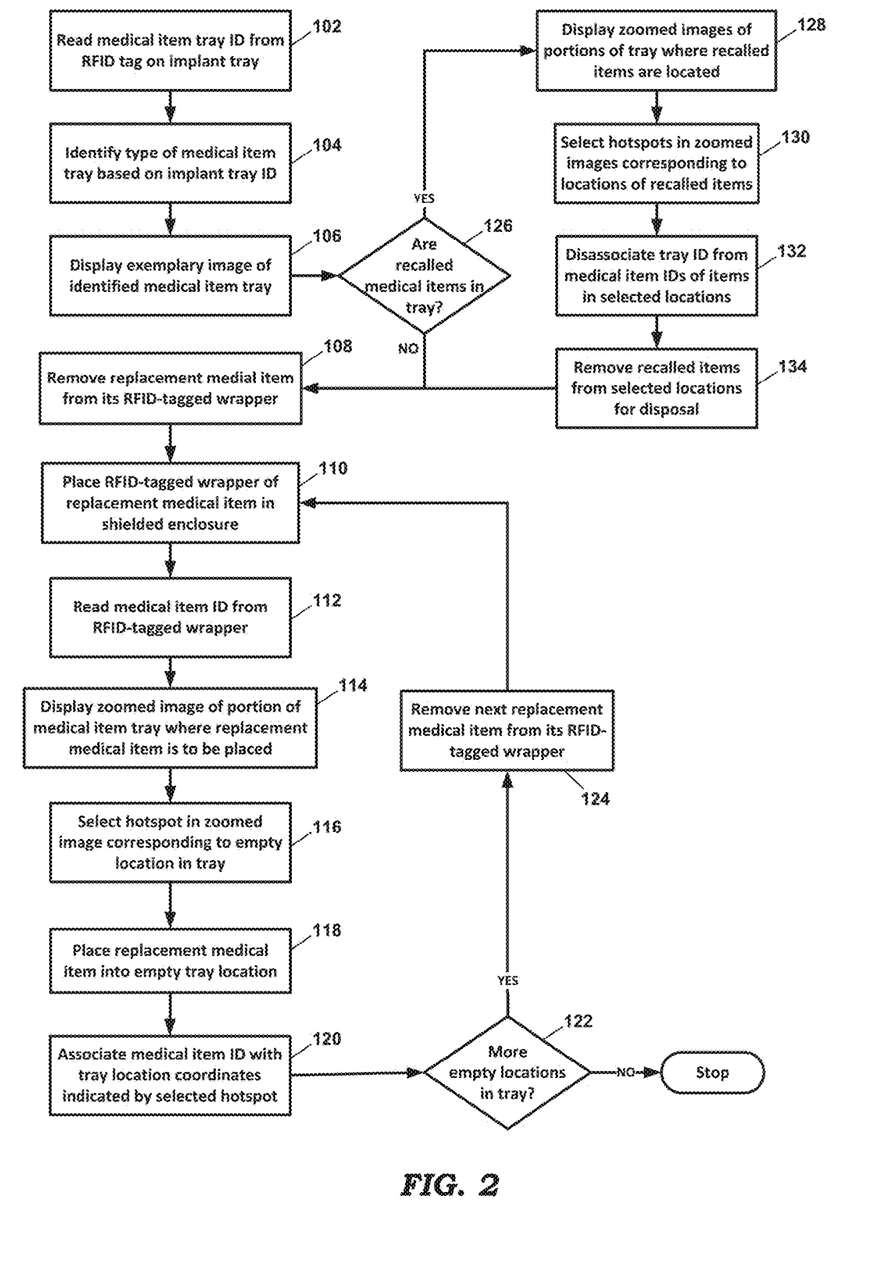
FIG. 2 depicts steps of a method for storing medical item identification information in association with location information indicating specific locations of medical items in a medical item tray.
Figure 3A:
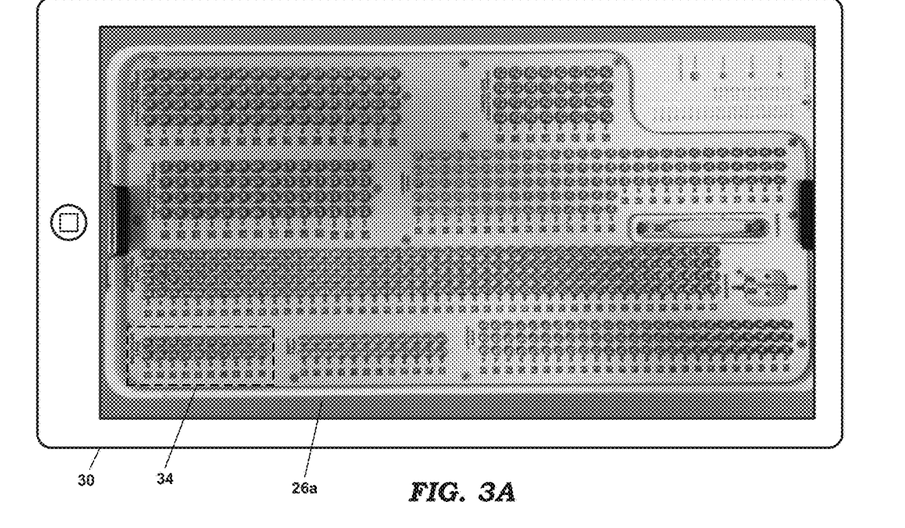
FIGS. 3A, 3B, 4A and 4B depict exemplary display screens indicating specific locations in a medical item tray in which particular medical items are to be placed.
Figure 4A:
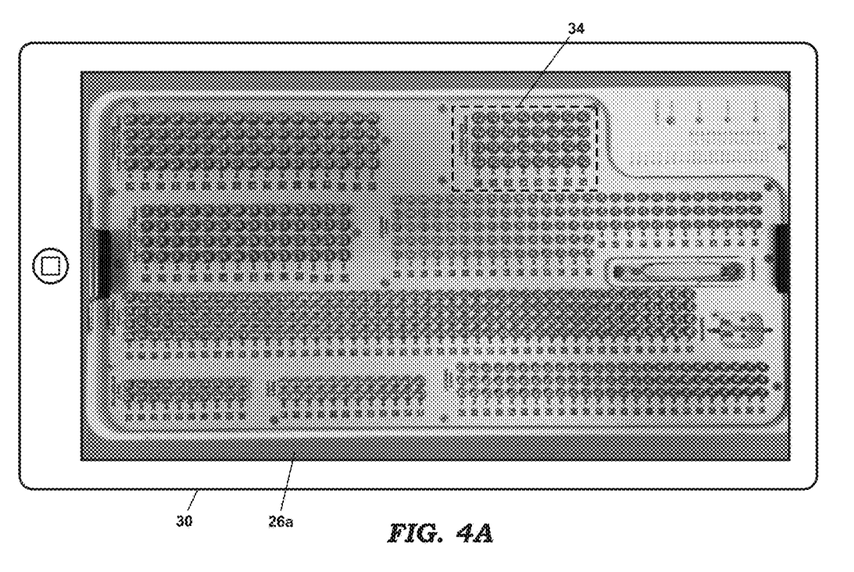

FIG. 2 depicts steps in a preferred embodiment of a method for storing medical item identification information in association with location information that indicates specific locations of specific medical items in a medical item tray. In the preferred embodiment, the method of FIG. 2 is implemented using the system depicted in FIG. 1. These steps may be performed as part of a process of refilling empty slots in a tray after various medical items from the tray were removed and used during a medical procedure. Initially, the identification information encoded in the device 24 on the tray 22 to be refilled is read and the tray's model number and serial number are acquired (step 102). In this embodiment, the model number identifies the type of tray (and perhaps the type of medical procedure in which it is used), and the serial number identifies the specific tray out of multiple trays of a particular type. Once the tray type is identified, the item information database 40 is accessed to load an image of the type of tray that corresponds to the tray's model number (step 104). As shown in the examples of FIGS. 3A and 4A, a full image 26a of the identified tray is initially displayed on the display device 36 of the supply room computer 30 (step 106).

Figure 3B:
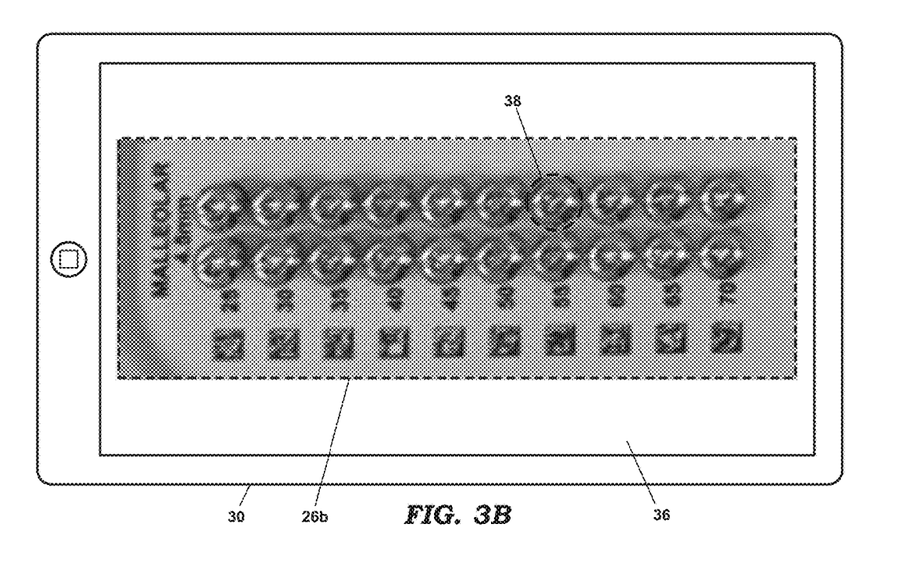
Figure 4B:
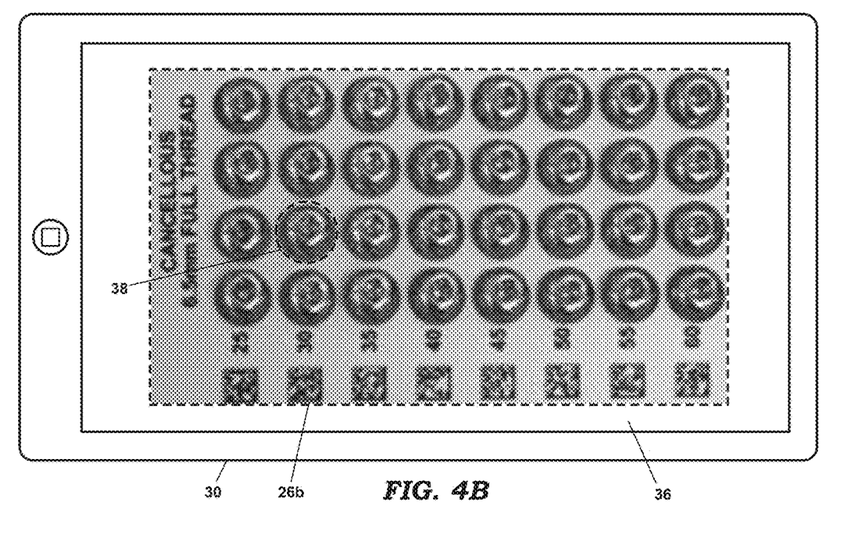

In some preferred embodiments, the item information database 40 is also accessed to determine whether the identified tray contains any medical items that have expired or been subject to a recall (step 126). If the tray contains any such items, one or more graphic boxes 34 appear within the full image 26a indicating one or more portions of the tray in which one or more expired or recalled items are located. The graphic boxes 34 are preferably animated in some way to attract the user's attention. In a preferred embodiment, within each box 34 is hotspot. As the word is used herein, a "hotspot" is a special area on the display screen 36 that provides for hyperlinking or for other graphic user interface (GUI) functions, such as re-direction, pop-up display, macro execution, etc. When a user touches or clicks on the hotspot within one of the boxes 34, the display 36 (or other user input device) generates a hotspot signal that causes the computer 30 to generate a zoomed image 26b of the portion of the tray within the selected box 34 is displayed on the screen 36 (step 128), as shown in FIGS. 3B and 4B.

Within each zoomed image 26b are one or more graphic circles 38 (or other shape) indicating specific slot locations in the tray 22 containing expired or recalled medical items that are to be removed from the tray 22 and discarded. The graphic circles 38 are preferably animated in some way to attract the user's attention. When the user touches or clicks on the hotspot within any one of the circles 38 (step 130), a command is executed that disassociates in the database 40 the serial number of the specific tray 22 from the serial number of the specific medical item at the location in the tray 22 designated by the circle 38 (step 132). At this point, the database 40 indicates that the corresponding location in the tray 22 is now empty. The user then physically removes the expired or recalled medical item from the slot in the tray 22 designated by the circle 38 and discards the item (step 134). Steps 130-134 are repeated until all expired and recalled items have been removed.

In a preferred embodiment, after all expired and recalled items have been removed from the tray 22, the user acquires from storage the medical items needed to resupply the tray 22. The following procedure is then performed, preferably one medical item at a time. The user removes the first replacement medical item from its wrapper 20 (step 108) and drops the empty wrapper 20 into the shielded enclosure 12 (step 110). Upon detection of the RFID tag on the empty wrapper 20, the RFID reader 28a decodes the item identification information, and the model number and serial number of the medical item that was in the wrapper are acquired (step 112). In this embodiment, the model number identifies the type of medical item (such as Malleolar 4.5 mm screw) and the serial number identifies the specific item out of multiple items of the same type.

The item information database 40 is accessed to determine the portion of the tray 22 in which the identified replacement medical item is to be placed, and a graphic box 34 appears in the full image 26a indicating that portion of the tray 22, examples of which are shown in FIGS. 3A and 4A. Again, the graphic box 34 is preferably animated in some way to attract the user's attention, and it contains a hotspot. When the user touches or clicks on the hotspot within the box 34, a zoomed image 26b of the portion of the tray within the selected box 34 is displayed on the screen 36 (step 114), examples of which are shown in FIGS. 3B and 4B.

Within each zoomed image 26b are one or more graphic circles 38 (or other shape) indicating one or more empty locations within the zoomed portion of the tray 22 in which the replacement medical item could be placed. Each graphic circle 38 is preferably animated in some way to attract the user's attention. The user inserts the replacement medical item into one of the empty slots in the tray 22 designated by the graphic circles 38 in the image 26b (step 118) and touches or clicks on the hotspot within the circle 38 corresponding to the slot into which the replacement item was just inserted (step 116). When the user touches or clicks on the hotspot within the circle 38 (step 116), a command is executed that associates in the database 40 the serial number of the specific replacement medical item with the serial number of the specific tray 22 and with the specific location in the tray 22 designated by the selected circle 38 (step 120). At this point, the database 40 indicates that this specific location in the tray 22 is now occupied by the specific medical item having the serial number decoded in step 112.

If there are more replacement items to be placed in more empty locations in the tray 22 (step 122), the user removes the next replacement medical item from its wrapper 20 (step 124) and steps 110 through 122 are repeated until all empty slots in the tray 22 have been filled.

In some embodiments, the RFID reader 28a decodes model and serial number information directly from the RFID tags attached to the wrappers. In alternative embodiments, the RFID reader 28a decodes a single identification number from each RFID tag, and the single identification number is cross-referenced in the database 40 to obtain the model number and serial number. Similarly, in some embodiments, the RFID reader 28b decodes model and serial number information directly from the RFID tag 24 attached to the tray 22. In alternative embodiments, the RFID reader 28b decodes a single identification number from the RFID tag 24 attached to the tray 22, and the single identification number is cross-referenced in the database 40 to obtain the model number and serial number of the tray 22. Accordingly, it will be appreciated that the invention is not limited to any particular process for obtaining model numbers and serial numbers of the tray or of the medical items.

In preferred embodiments, some of the computer processing steps described above and depicted in FIG. 2 are executed by the supply room computer 30, and some are executed by the medical item inventory computer 44. In some embodiments, all of the computer processing steps described above and depicted in FIG. 2 are executed by the supply room computer 30. Accordingly, it will be appreciated that the invention is not limited to any particular computer or combination of computers executing the process steps.

In preferred embodiments, particular locations of slots in a medical item tray are specified by location coordinates. For example, each slot location in the tray may be designated using an X-Y coordinate system, where the values of X and Y are dimensions, such as in inches or centimeters, from a origin location (0, 0) on the tray. Alternatively, each slot location in the tray may be designated using a row-column designation, such as column 25, row 3. Accordingly, it will be appreciated that the invention is not limited to any particular scheme for assigning location coordinates to slots in the medical item tray.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for storing medical item identification information in association with information indicating locations at which medical items are disposed in a medical item tray, the method comprising:
    (a) acquiring tray identification information from a first identification device attached to the medical item tray;
    (b) displaying a first image on a display device, wherein the first image depicts a medical item tray of a type indicated by the tray identification information;
    (c) acquiring medical item identification information from a second identification device attached to a medical item that is to be placed in the medical item tray or to a wrapper of the medical item;
    (d) based on the medical item identification information, acquiring tray zone information indicating a zone of the medical item tray in which the medical item is to be placed; and
    (e) displaying a second image on the display device, wherein the second image depicts a portion of the first image corresponding to the zone of the medical item tray indicated by the tray zone information.

2. The method of claim 1 further comprising:
    (f) selecting a hotspot in the second image corresponding to a location in the medical item tray in which the medical item is to be placed;
    (g) placing the medical item into the location in the medical item tray corresponding to the hotspot selected in step (f); and (h) in a medical item information database, associating the medical item identification information with:
the tray identification information; and
tray coordinate information corresponding to the location.

3. The method of claim 2 further comprising repeating steps (c) through (h) for additional medical items that are to be placed in available locations in the medical item tray.

4. The method of claim 1 wherein the first identification device comprises an RFID tag.

5. The method of claim 1 wherein step (a) further comprises acquiring the tray identification information from a medical item information database based on information contained in the first identification device.

6. The method of claim 1 wherein the second identification device comprises an RFID tag attached to medical item or the wrapper of the medical item.

7. The method of claim 6 wherein step (c) comprises disposing the wrapper of the medical item in a shielded enclosure containing an RFID antenna, and reading the medical item identification information from the RFID tag using the RFID antenna within the shielded enclosure.

8. The method of claim 1 wherein step (c) further comprises acquiring the medical item identification information from a medical item information database based on information contained in the second identification device attached to the medical item or the wrapper of the medical item.

9. The method of claim 1 wherein step (e) further comprises displaying the second image as a zoomed-in portion of the first image.

10. The method of claim 2 further comprising displaying one or more graphic indicators in the second image to designate one or more hotspots.

11. A method for storing medical item identification information in association with information indicating locations at which medical items are disposed in a medical item tray, the method comprising:
(a) acquiring tray identification information from an identification device attached to the medical item tray;
(b) displaying a first image on a display device, wherein the first image depicts a medical item tray of a type indicated by the tray identification information;
(c) accessing a medical item information database to determine whether any medical item disposed in the medical item tray identified by the tray identification information has been recalled or is beyond an expiration date;
(d) based on the medical item identification information, acquiring tray zone information from the medical item information database, the tray zone information indicating a zone of the medical item tray in which is located a recalled or expired medical item;
(e) displaying a second image on the display device, wherein the second image depicts a portion of the first image corresponding to the zone of the medical item tray indicated by the tray zone information;
(f) displaying a graphical indicator in the second image, wherein the graphical indicator designates a hotspot in the second image corresponding to a location in the medical item tray in which a recalled or expired medical item is disposed;
(g) selecting the hotspot designated by the graphical indicator;
(h) removing the recalled or expired medical item from the medical item tray; and
(i) in the medical item information database, disassociating the medical item identification information of the recalled or expired medical item from tray coordinate information corresponding to the location designated by the hotspot selected in step (g).

12. An apparatus for storing medical item identification information in association with information indicating locations at which medical items are disposed in a medical item tray, the apparatus comprising:
one or more readers that are operable to acquire
tray identification information from a first identification device attached to the medical item tray, and
medical item identification information from a second identification device attached to a medical item that is to be placed in the medical item tray or to a wrapper of the medical item;
a medical item information database for storing medical item identification information in association with tray identification information and tray zone information, wherein the tray zone information indicates particular zones of the medical item tray in which particular medical items are to be placed;
one or more computer processors in communication with the one or more readers and the medical item information database, the one or more computer processors for processing the medical item identification information, the tray identification information and the tray zone information, the one or more computer processors operable to execute instructions to
generate a first image that depicts a medical item tray of a type indicated by the tray identification information, and
generate a second image that depicts a portion of the first image corresponding to a zone of the medical item tray indicated by the tray zone information; and
a display device in communication with the one or more computer processors, the display device operable to display the first and second images.

13. The apparatus of claim 12 wherein the one or more computer processors are operable to execute instructions to generate the second image as a zoomed-in portion of the first image.

14. The apparatus of claim 12 wherein the second identification device attached to the wrapper of the medical item comprises an RFID tag, the apparatus further comprising:
a shielded enclosure having an internal space for receiving the wrapper of the medical item, the shielded enclosure configured to attenuate radio frequency signals emanated from RFID tags disposed outside the shielded enclosure to levels that are substantially undetectable within the internal space;
an RFID antenna disposed within the internal space of the shielded enclosure, the RFID antenna for receiving a radio frequency signal emanated from the RFID tag attached to the wrapper disposed within the internal space, wherein the radio frequency signal contains the medical item identification information encoded in the RFID tag; and
the one or more readers including an RFID reader electrically connected to the RFID antenna, the RFID reader for decoding the medical item identification information contained in the radio frequency signal emanated from the RFID tag.

15. The apparatus of claim 12 further comprising:
the one or more computer processors operable to execute instructions to generate the second image including a hotspot corresponding to a location in the medical item tray in which the medical item is to be placed;

a user input device in communication with the one or more computer processors, the user input device for selecting the hotspot in the second image to generate a hotspot signal; and the one or more computer processors operable to execute instructions based on the hotspot signal to communicate with the medical item information database to cause the medical item identification information to be associated with the tray identification information and tray coordinate information corresponding to the location.

16. The apparatus of claim 15 wherein the user input device comprises a touch screen incorporated into the display device.

17. The apparatus of claim 15 wherein the one or more computer processors are operable to execute instructions to generate a graphic indicator that is displayed in the second image to designate the hotspot.

18. The apparatus of claim 15 wherein the tray coordinate information comprises X-Y coordinates or row-column coordinates.

* * * * *